United States Patent
Baek

(10) Patent No.: US 7,290,441 B2
(45) Date of Patent: *Nov. 6, 2007

(54) MICRO SLIT VISCOMETER WITH MONOLITHICALLY INTEGRATED PRESSURE SENSORS

(75) Inventor: Seong-Gi Baek, Pleasanton, CA (US)

(73) Assignee: Rheosense, Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/078,015

(22) Filed: Mar. 11, 2005

(65) Prior Publication Data

US 2005/0183496 A1    Aug. 25, 2005

Related U.S. Application Data

(63) Continuation-in-part of application No. 10/286,602, filed on Oct. 31, 2002, now Pat. No. 6,892,583.

(60) Provisional application No. 60/335,375, filed on Oct. 31, 2001, provisional application No. 60/552,289, filed on Mar. 11, 2004.

(51) Int. Cl.
*G01N 11/08* (2006.01)
*G01N 21/00* (2006.01)

(52) U.S. Cl. .................... 73/54.09; 73/54.16; 73/54.43; 73/54.39

(58) Field of Classification Search ............... 73/54.09, 73/54.43, 54.39, 54.14, 54.16
See application file for complete search history.

(56) References Cited

U.S. PATENT DOCUMENTS

| 4,241,602 A | 12/1980 | Han et al. |
| 4,624,132 A | 11/1986 | Parnaby et al. |
| 5,029,479 A * | 7/1991 | Bryan .......................... 73/721 |
| 5,058,435 A * | 10/1991 | Terry et al. .................... 73/727 |
| 5,202,939 A | 4/1993 | Belleville et al. |

(Continued)

OTHER PUBLICATIONS

Dziuban, J.A. et al.; "Silicon optical pressure sensor"; Sensors and Actuators A (Physical); Apr. 1992, pp. 628-631; vol. A32, No. 1-3; Switzerland.

(Continued)

*Primary Examiner*—Michael Cygan
(74) *Attorney, Agent, or Firm*—Thorpe North & Western, LLP

(57) ABSTRACT

An improved micro slit viscometer includes a combined micrometer depth rectangular slit flow channel with monolithically integrated multiple pressure sensors in the flow channels and a pumping system that injects a test sample to the channel at a desired flow rate. Pressure sensing diaphragm of the monolithically integrated pressure sensors is smooth to minimize the flow disturbance thereby measuring accurate local pressures. With the measurement of the pressures at various locations of the channel the true viscosity of test sample can be calculated. The viscometer may consist of multiple flow channels and thus the true viscosity at multiple shear rates can be measured simultaneously for a given flow rate thereby obtaining a full viscosity curve as a function of shear rate of non-Newtonian liquids in a much faster manner. The viscometer needs only a miniscule amount of sample, which minimizes a waste of test material. The flow channels and the monolithically integrated pressure sensors are fabricated using microfabriaction processes on wafers and combined, which greatly reduce the production costs.

26 Claims, 16 Drawing Sheets

U.S. PATENT DOCUMENTS

Figure 1:
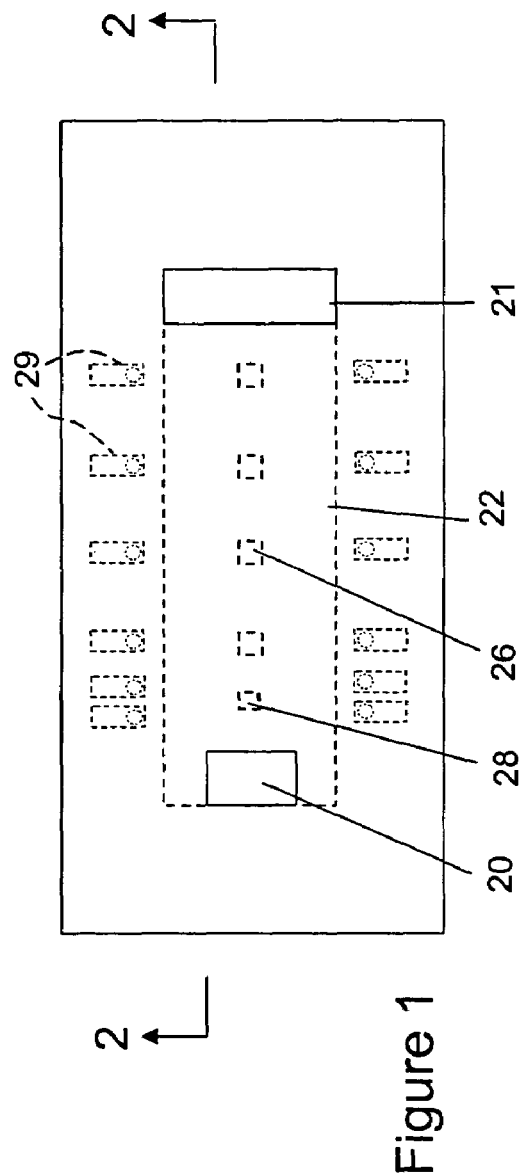

| | | |
|---|---|---|
| 5,225,959 A | 7/1993 | Stearns |
| 5,392,117 A | 2/1995 | Belleville et al. |
| 5,485,753 A | 1/1996 | Burns et al. |
| 5,663,503 A | 9/1997 | Dam et al. |
| 5,983,727 A | 11/1999 | Wellman et al. |
| 6,062,088 A | 5/2000 | Ingrisch et al. |
| 6,078,706 A | 6/2000 | Nau et al. |
| 6,085,596 A | 7/2000 | Jensen et al. |
| 6,725,725 B1 | 4/2004 | Werner et al. |
| 6,892,583 B2 * | 5/2005 | Baek .......................... 73/715 |

OTHER PUBLICATIONS

Wagner, C. et al.; "Optical pressure sensor based on a Mach-Zehdner Interferometer integrated with a lateral a-Si:H p-i-n photodiode"; IEEE Photonics Technology Letters; Oct. 1993, pp. 1257-1259; vol. 5, No. 10; USA.

Chan M.A. et al.; "A micromachined pressure sensor with fiber-optic interferometric readout"; Sensors and Actuators A (Physical); May 1994, pp. 196-201; vol. A42, No. 1-3; Switzerland.

Lee, S.B. et al.; "A micromachined interferometer for dynamic high-pressure sensing (in automotive applications)"; Sensors; Jun. 1996, pp. 31-32 and 35-36; vol. 13, No. 6; Helmers Publishing, USA.

FISO Technologies; "Product Data Sheet, FOP-M In-Vivo Pressure Sensor", 2 pages.

FISO Technologies; "Technical Note Series, Fiber-Optic Pressure Transducer", 4 pages.

* cited by examiner

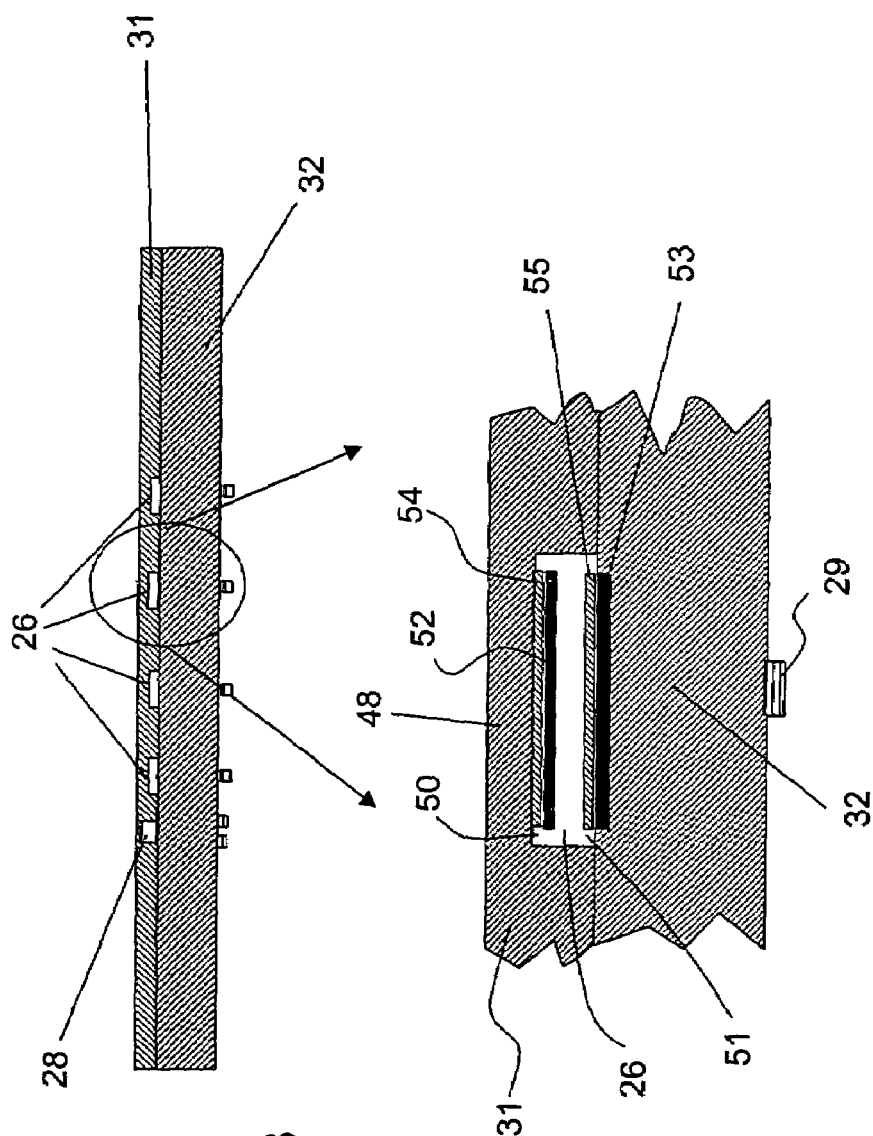

MICRO SLIT VISCOMETER WITH MONOLITHICALLY INTEGRATED PRESSURE SENSORS

RELATED APPLICATIONS

This application is a continuation-in-part of U.S. patent application Ser. No. 10/286,602, filed Oct. 31, 2002, now U.S. Pat. No. 6,892,583, which claimed the benefit of provisional application Ser. No. 60/335,375, filed Oct. 31, 2001, both entitled "Pressure Sensing Device For Rheometers." This application also claims the benefit of U.S. Provisional Patent Application Ser. No. 60/552,289, filed Mar. 11, 2004, and entitled "Micro Slit Viscometer with Monolithically Integrated Pressure Sensors." All of the above applications are incorporated herein by reference.

BACKGROUND OF INVENTION

Field: This invention is in the field of miniature devices that measure true viscosities of liquid.

State of the art: Viscosity is a measure of resistance of liquid to flow and its value depends on the rate of deformation for Non-Newtonian liquids as described in Dynamics of Polymeric Liquids, Vol. 1, 1987 authored by R. B. Bird, R. C. Armstrong, and O. Hassager. The rate of deformation is given by a shear rate in a unit of $(\text{time})^{-1}$. The viscosity measured at a known shear rate is "true" viscosity. The dependence of the true viscosity on shear rate is a viscosity curve which characterizes material and is an important factor to consider for efficient processing. But in many cases viscosity is measured under ill-defined test conditions so that shear rate can not be known or calculated. Under ill-defined conditions, the measured viscosity value is only "apparent". Since the true viscosity is measured at a known shear rate, the true viscosity is universal whereas the apparent viscosity is not. Instead, the apparent viscosity depends on the measuring system. For example, as a common practice, a torque of a spindle immersed in a sea of test liquid is measured while the spindle is being rotated at a constant speed. In this case the torque value only yields an apparent viscosity since the test condition is ill defined and a shear rate is not known. At best, the apparent viscosity can be measured as a function of the rotational speed of the spindle. The rotational speed of the spindle can be, in fact, correlated with the shear rate only if a "constitutive equation" for the test liquid is known. However, a "constitutive equation" is not known for almost all Non-Newtonian liquids. Therefore, true viscosity can not be measured with ill-defined test conditions for most non-Newtonian liquids.

The methods that give only apparent viscosities have been developed and used for quality controls in manufacturing and material characterization. Various on-line viscometers have been designed for real time viscosity measurement. Prior art U.S. Pat. Nos. 5,317,908 (Fitzgerald et al.) and U.S. Pat. No. 4,878,378 (Harada) are concerned with systems that measure apparent viscosities for process controls. Prior art U.S. Pat. No. 6,393,898 (Hajduk et al.) describes a system that measures many test liquids simultaneously. These viscometers measure apparent viscosities. However, because of the non-universality of the apparent viscosity measurement, a correlation of the apparent viscosity of a specific sample measured with a specific method to the true viscosity has to be found separately, when desired. Fundamental development of formulations or materials requires a true viscosity measurement. Also, the design of processing equipments and accessories such as dies, molds, extrusion screws, etc., require knowledge of the true viscosity of the materials. However, the apparent viscosity measurement has been used for a quick test as an indication since it is easier and faster to measure and often more economical. The true viscosity is more difficult to get and can be only measured with a few types of instruments: rheometers and capillary viscometers. The rheometers impose a precise and known shear rate on test samples thereby measuring true viscosities. The rheometers are versatile and equipped to measure other properties. Therefore they are usually expensive. Usually large amounts of sample are required for viscosity measurement with rheometers. Also, the rheometers are not well suited for on-line applications. Circular capillary viscometers are another type of instrument that can measure apparent and true viscosities depending on whether a proper compensation is taken into account. The capillary viscometer needs a measurement of pressure drop along the capillary for determining viscosity. Since the capillary is circular, only the pressure at the entrance and exit can be measured. Because of this limitation, the capillary viscometer measures only apparent viscosity unless the entrance effect is corrected by using two different capillaries with different length to diameter ratios. However, the use of two capillaries makes the viscometer bulky and measurements time consuming. Capillary viscometers are shown in the prior art: for example in U.S. Pat. No. 6,575,019 (Larson); U.S. Pat. No 4,920,787 (Dual et al.); U.S. Pat. No. 4,916,678 (Johnson et al.); and U.S. Pat. No. 4,793,174 (Yau). Microfluidic viscometers are also disclosed in prior art: for example in U.S. Pat. No. 6,681,616 (Michael Spaid et al.); and 20030182991 (Michael Spaid et al.). Residence time of a marker in a fluidic channel is used to measure the viscosity, which is not a true viscosity unless the test liquid is Newtonian.

Rectangular slit viscometers relevant to the current invention are also used to measure the true viscosity and they are well described in Rheology in Polymer Processing, 1976, authored by C.D. Han. In these viscometers, test liquid flows inside of a rectangular slit flow channel and local pressures along the flow channel are measured with deployed pressure sensors for a given flow rate. In contrast to the capillary viscometer, the inside of the slit is flat so that pressures in the slit can be measured with pressure sensors mounted in the slit. The positions of the pressure sensors have to be sufficiently inside of the flow channel so that pressures of a fully developed flow are measured. From the pressure measurement, wall shear stress can be calculated. As the flow rate is varied, shear rate can be varied. From the measurement of wall shear stress at different shear rates, true viscosities are calculated using the well known Weissenberg-Rabinowitsch correction, which is much simpler than using two separate capillaries in case of using circular capillary viscometers. These viscosity measurements however are only simpler if the width of the flow channel is sufficiently larger than the depth of the flow channel. These slit viscometers need pumping systems for a precise control of the volumetric flow rate of test liquid. Frequently, the slit viscometers are used as an attachment to extruders as the liquids flow out of the extruders. In current practice, the pressure sensors are mounted individually to the plate flush enough to measure unperturbed pressures. However, it is very well known that a perturbation of flow significantly influences pressure measurement, particularly for viscoelastic non-Newtonian liquids. Any slight surface roughness due to the mounting of the pressure sensors may be a source of test sample deposition which degrades long term performance. Mounting of individual pressure sensors to eliminate surface roughness is difficult. Therefore, the measurement accuracy is often compromised depending on how well the individual pressure sensors are mounted in the flow channel. It has been found that the problems described above can be overcome with monolithically integrated pressure sensors in micro slit flow channels. With a single slit geometry, the shear rate can be only changed by the change of volumetric flow rate controlled by the pumping system. Most current slit viscometers are made individually with conventional machining processes, and are made for relatively large samples. Therefore, these conventional slit viscometers are not appropriate for measuring viscosities of test samples that are only available in a small quantity. Use of a micro slit flow channel with monolithically integrated pressure sensors can be tremendously advantageous. The micro slit viscometers allow the employment of microfabrication processes used to make micro chips and therefore these micro slit viscometers can be made in large quantity on a single wafer. This invention therefore makes the micro slit viscometers extremely cost-effective.

SUMMARY OF INVENTION

According to the current invention, a significantly smooth interior surface of a pressure sensing area is ensured by fabricating a monolithic array of pressure sensors and combining it with separately micro-fabricated flow channels. The smooth interior surface ensures that the slit flow is less perturbed and the accurate local pressures are measured and the interior surface is less likely damaged by a deposition of test materials. The slit flow channel is constructed in a micrometer scale so that only a miniscule amount of sample is required for viscosity measurement. Additionally, the pressure sensors and flow channels are fabricated on wafers using batch microfabrication processes of Micro-Electro-Mechanical Systems. Such a batch wafer process makes many identical parts at the same time and thereby reduces manufacturing costs of the micro viscometers.

Advances in microfabrication and micromachining processes enable the miniaturization of sensitive solid-state pressure sensors. Such a reduction in size allows in turn the densification of functionalities. Also the technical advances in microfabrication makes tailoring of pressure sensor sensitivity easier along with improvements in read out circuit designs. These improvements allow the tailoring of the micro viscometers to various purposes and for measuring wide ranges of viscosity.

In a preferred embodiment of the invention, the slit viscometer includes a flow cell and a pumping system capable of causing flow in a controlled manner. The flow cell further consists of a microfabricated flow channel (or channels) with an order of micrometer in depth for flow and monolithic pressure sensor arrays. Preferably the depth of the channel or channels is in the order of one micrometer, the length of the channel is longer than one hundred micrometers, and the width is wider than ten micronmeters. The flow channels are fabricated on a wafer in a known batch process. The monolithic pressure sensor arrays are also fabricated on a wafer or wafers. The microfabricated wafer with many flow channels is combined with the microfabricated wafer with many monolithic pressure sensor arrays in a known manner. The combined wafer has many flow cells, which are further diced to separate individual flow cells. In the slit viscometer, a test liquid is pumped to flow from one end of the flow channel to the other end and resulting pressure drop along the flow channel is measured.

A preferred method is to form the flow channel by etching wafers such as silicon (Si), Galum Arsenide (GaAs), borosilicate (Pyrex 7740), or derivatives of these materials in a known manner.

A preferred fabrication method to form pressure sensors is to form a plurality of cavities on a plate so that the smooth measuring surface of the plate extends over the cavities to form an end of the cavity which will deform slightly in response to pressure applied to the smooth surface over the cavity. A single and simple detection mechanism is formed on each cavity to provide a measurement of pressure applied by the liquid under test against the surface over the cavity. The detection mechanism is capacitive, piezo-resistive, or optical.

The primary object of the present invention is to provide a micro slit flow viscometer consisting of flow channels combined with monolithic pressure sensor arrays to measure true viscosities with a miniscule amount of sample. Another objective of this invention is that the flow channels and pressure sensors are fabricated on wafers commonly used in microfabrication and they are combined in order to mass produce viscometers in a cost effective manner.

THE DRAWINGS

Figure 2:
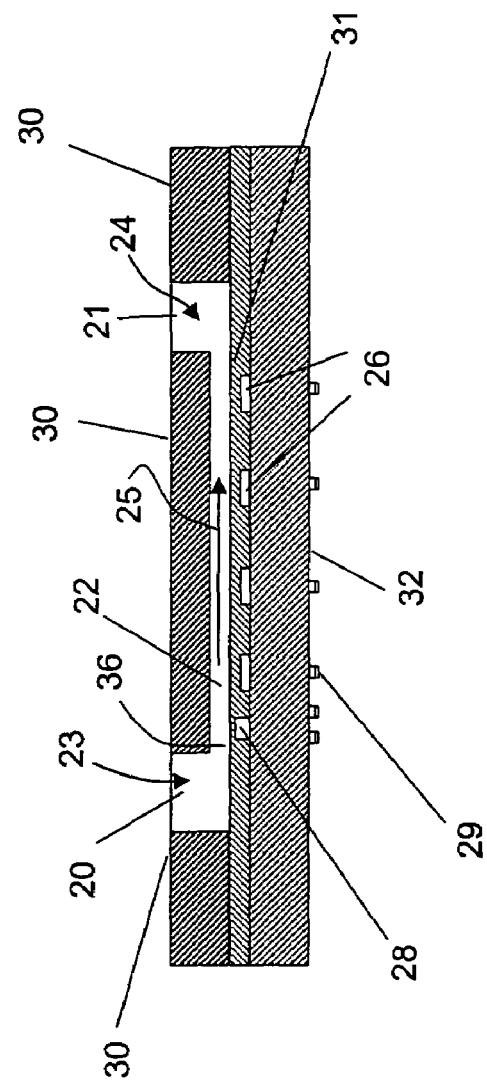
Figure 3:
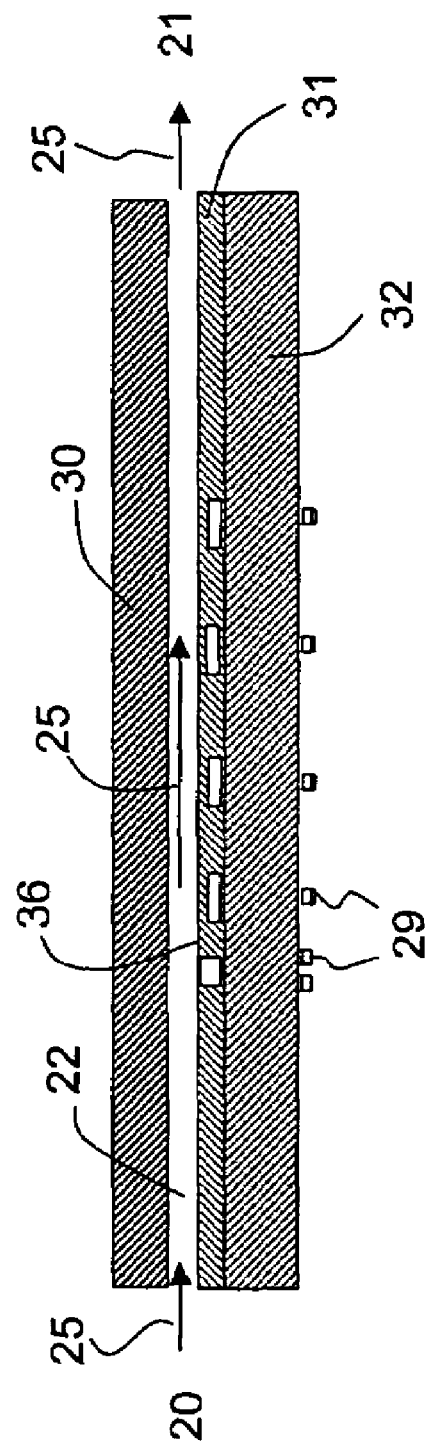
Figure 4:
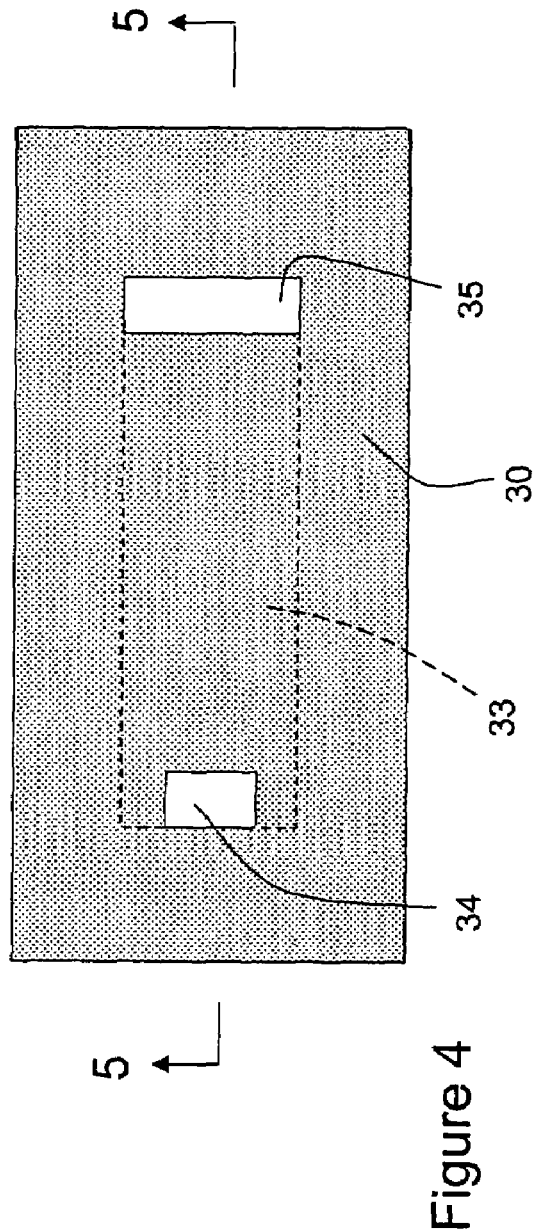
Figure 5:
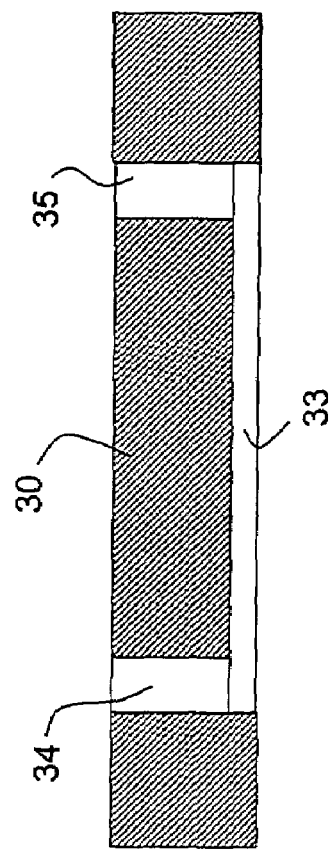
Figure 6:
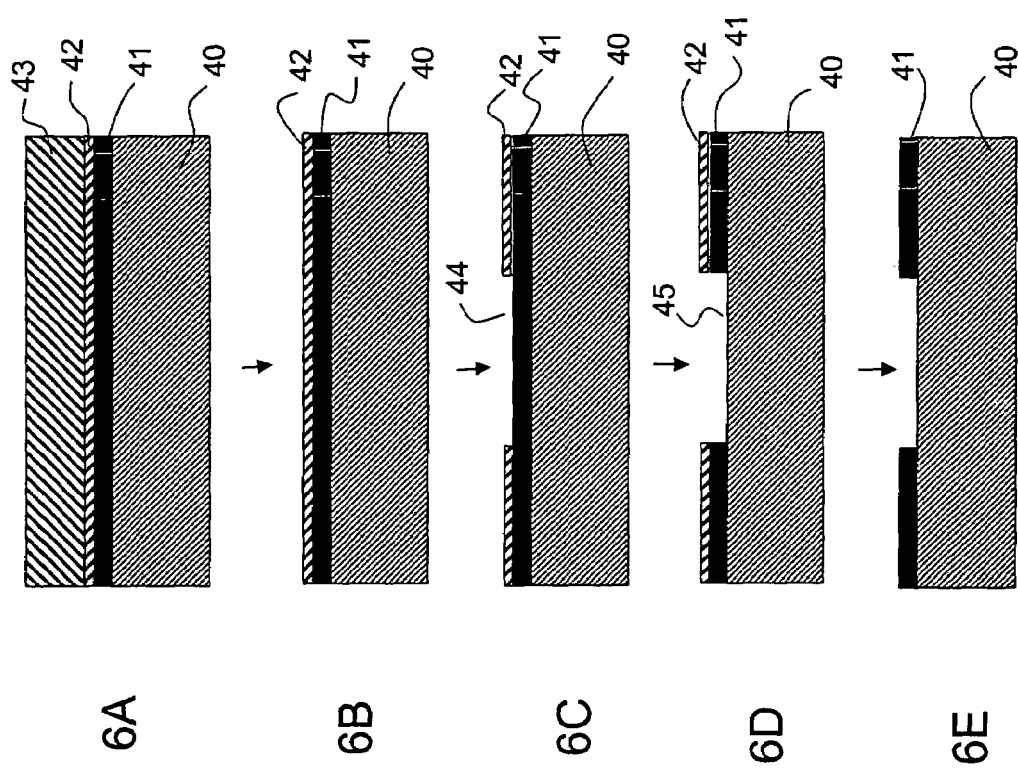
Figure 7:
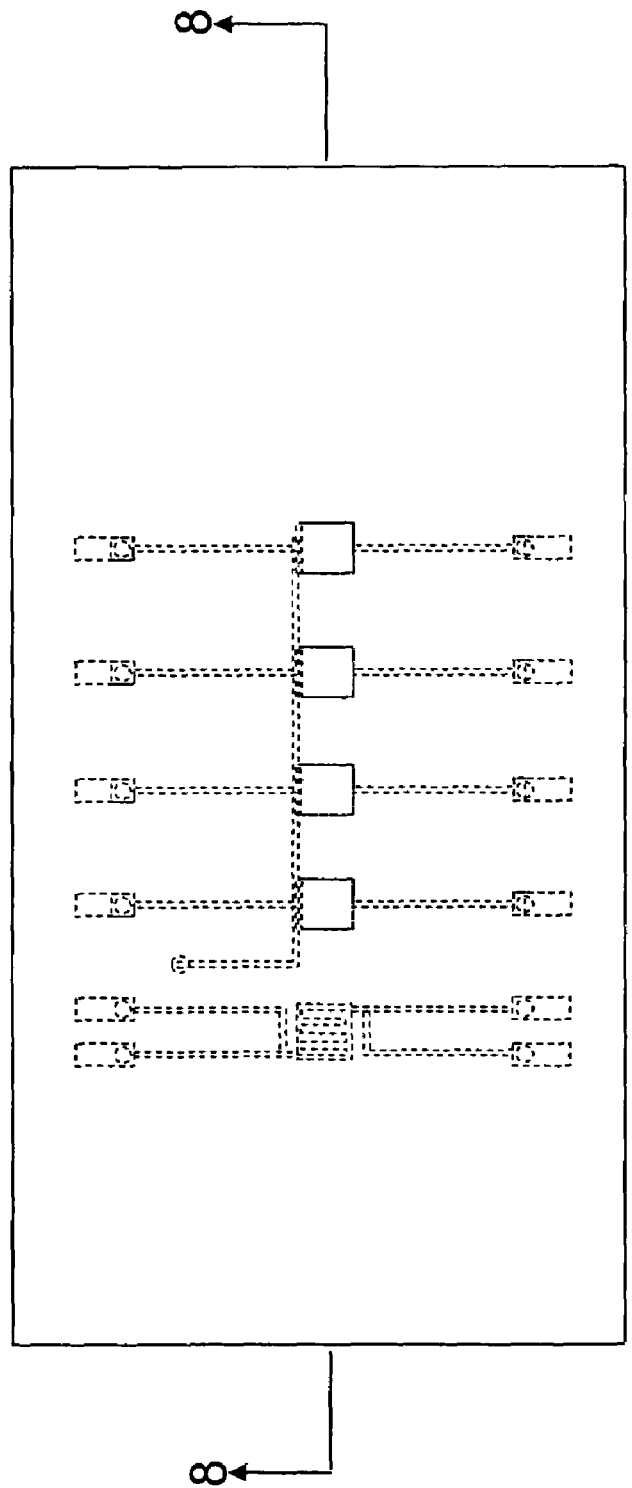
Figure 10:
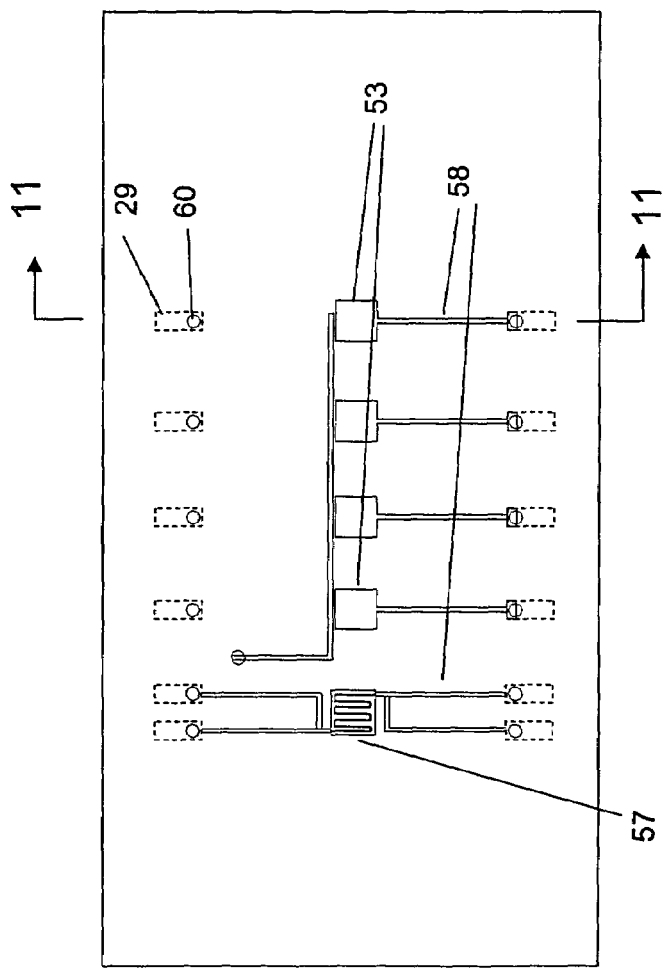
Figure 11:
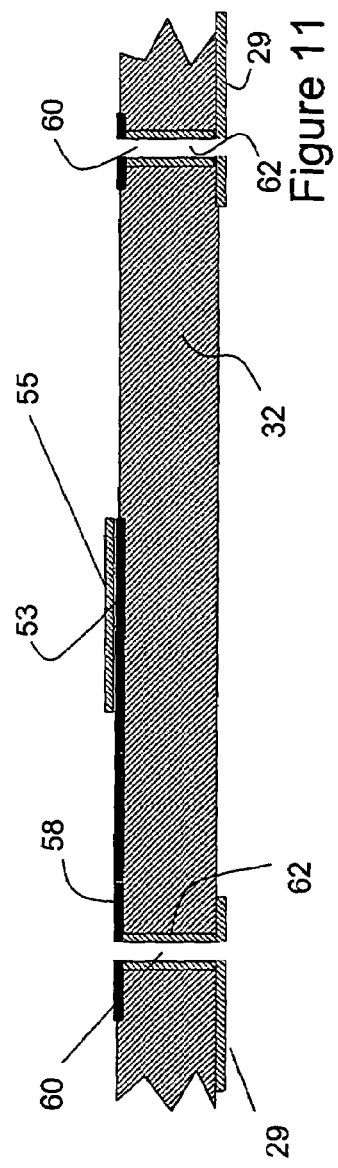
Figure 12:
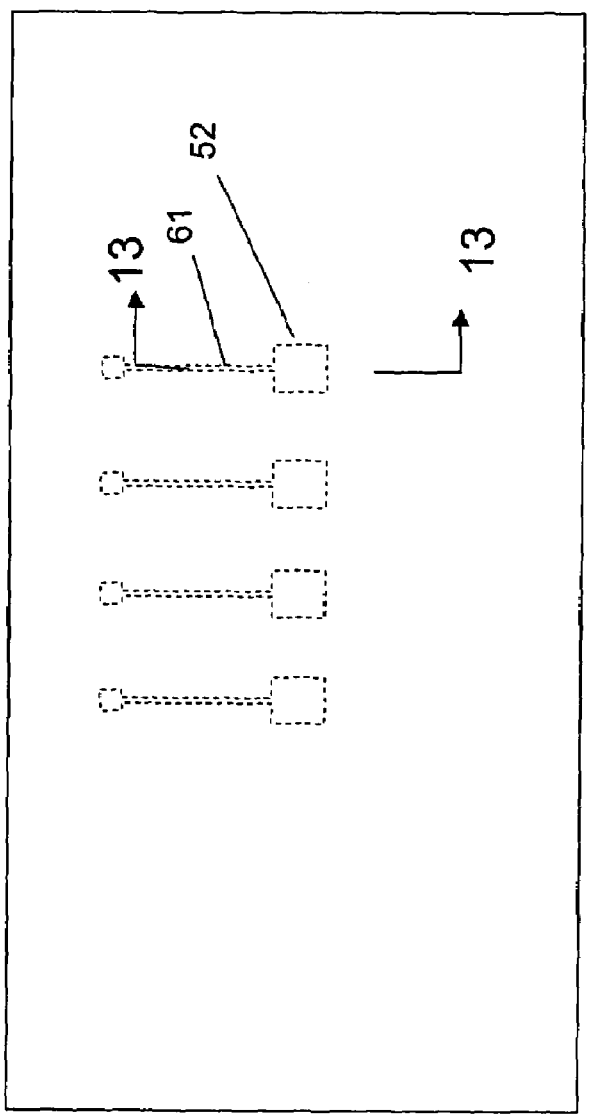
Figure 13:
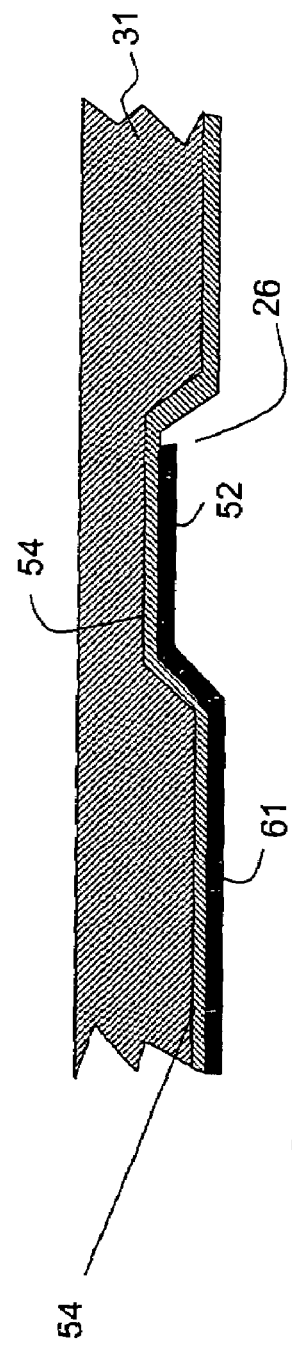
Figure 14:
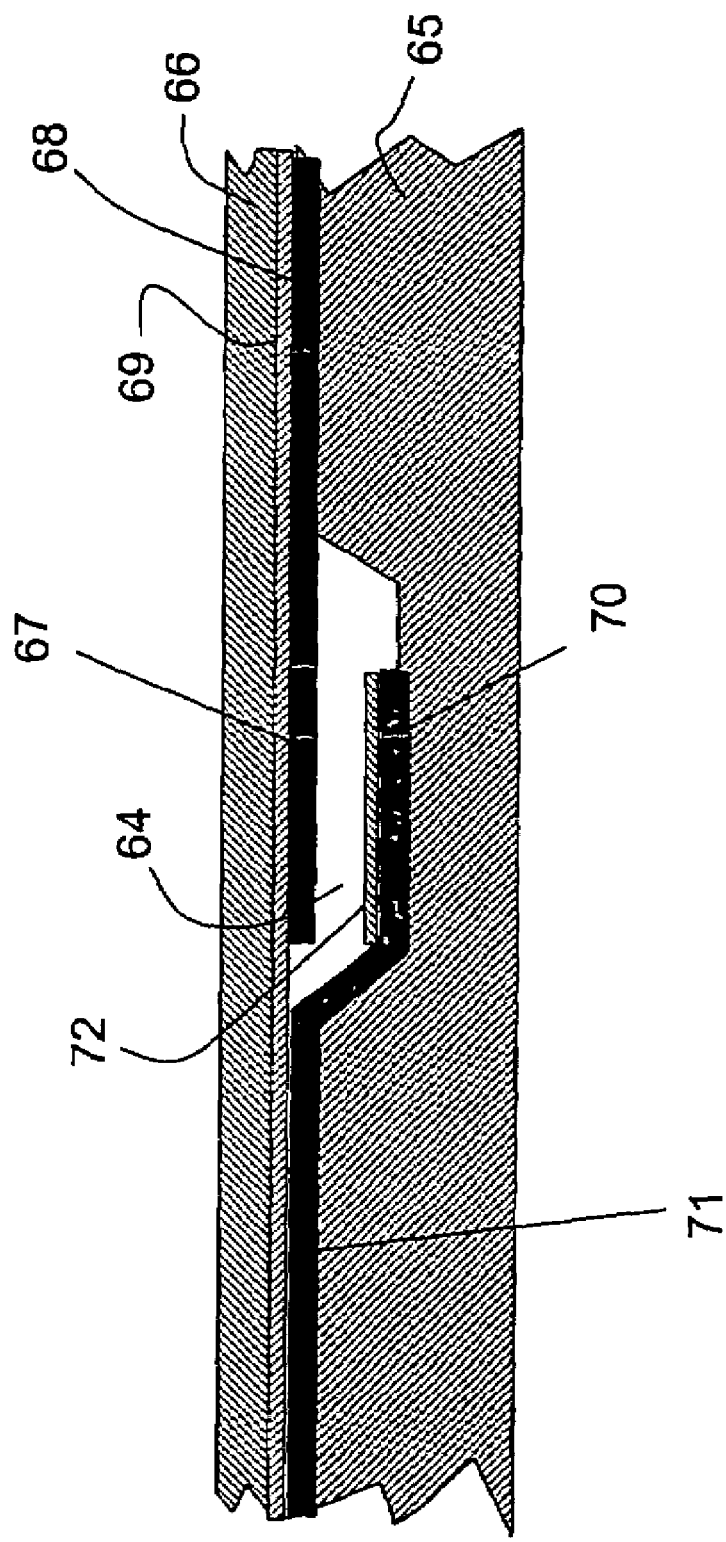
Figure 15:
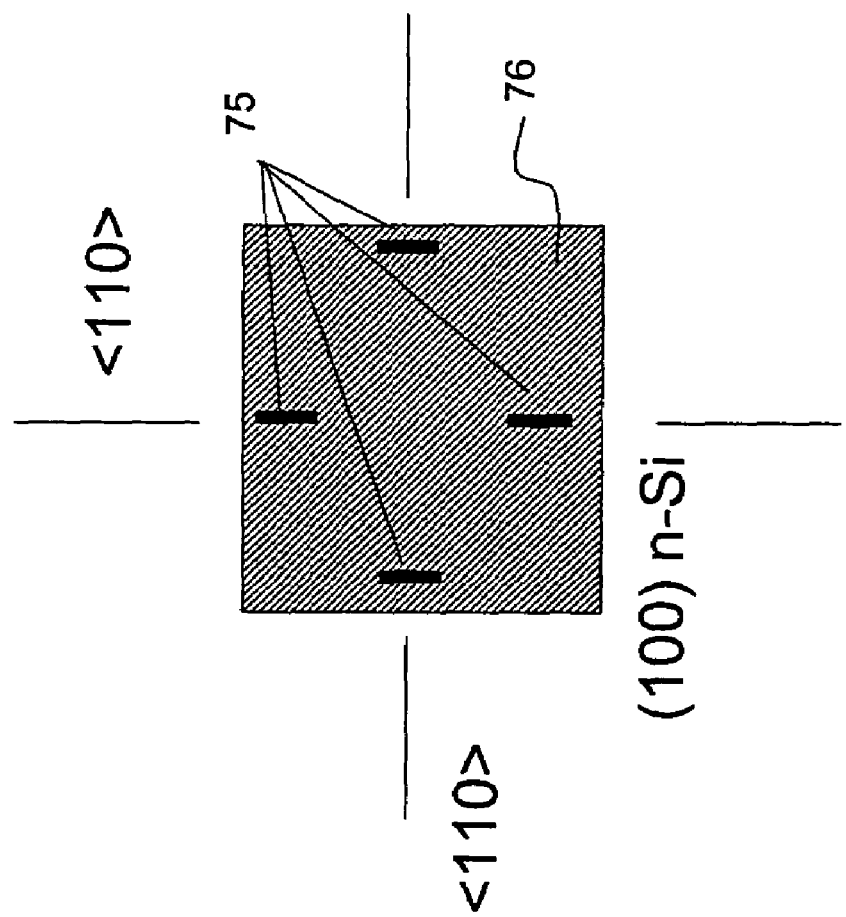
Figure 16:
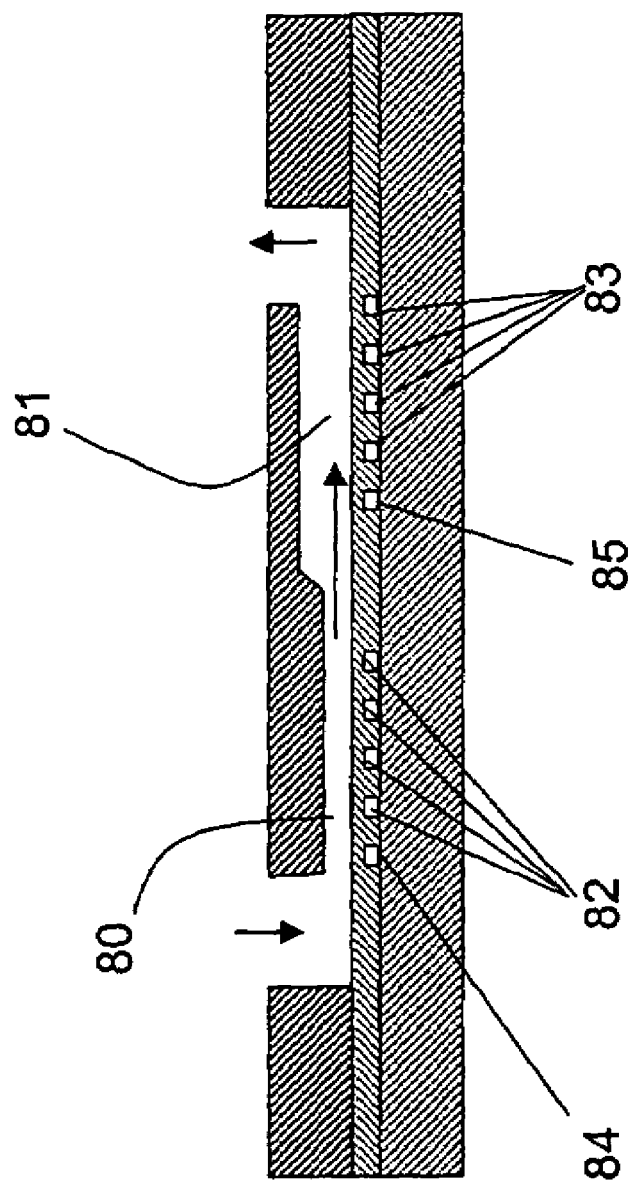
Figure 17:
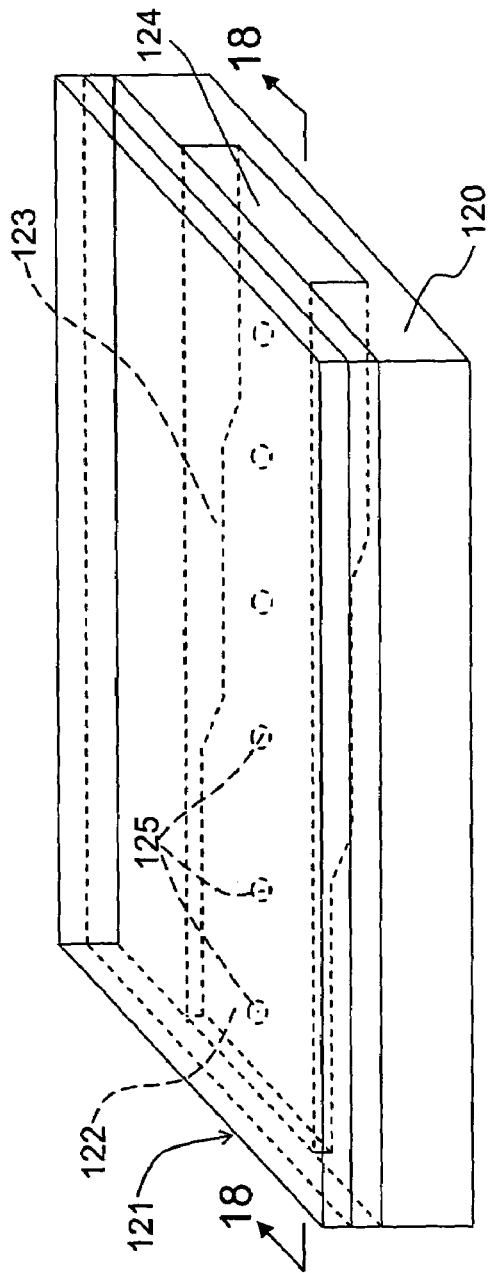
Figure 18:
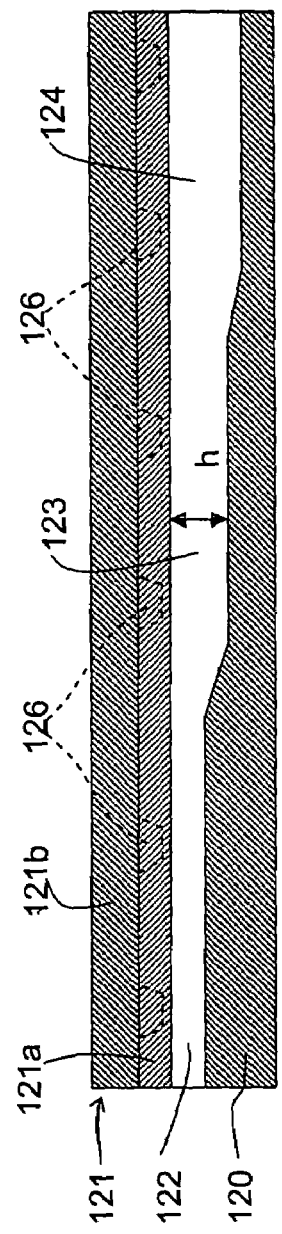
Figure 19:
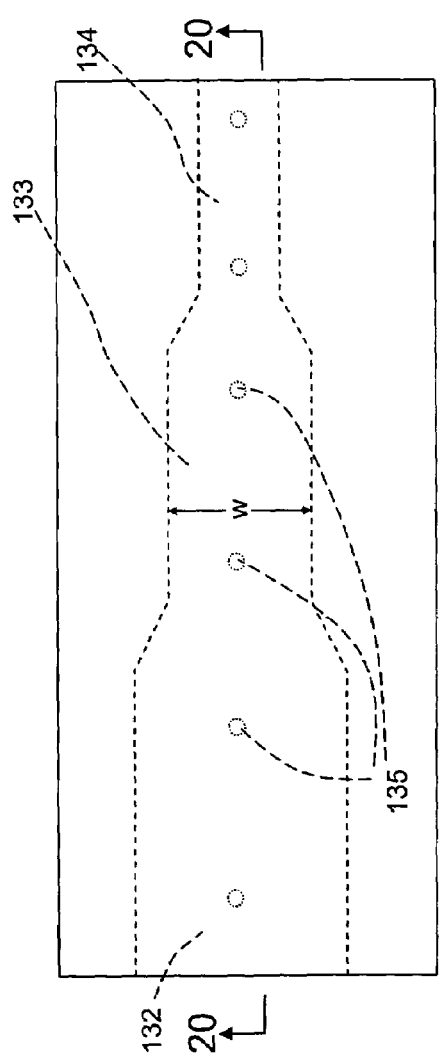
Figure 20:
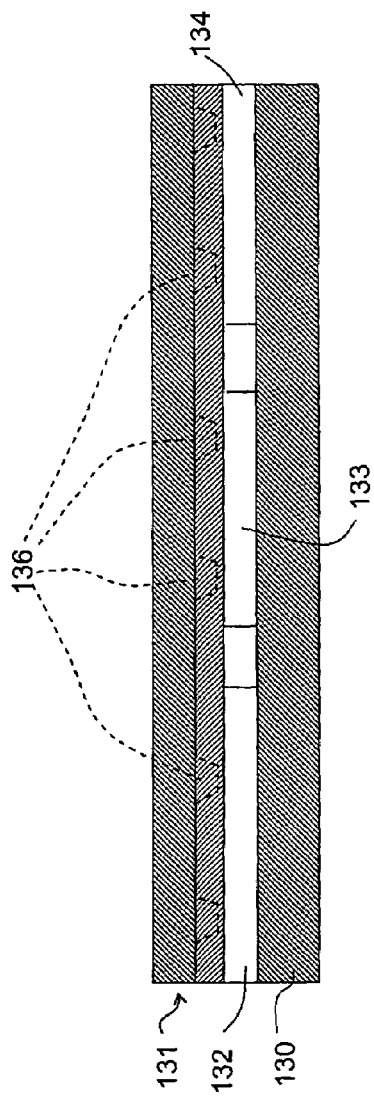
Figure 21:
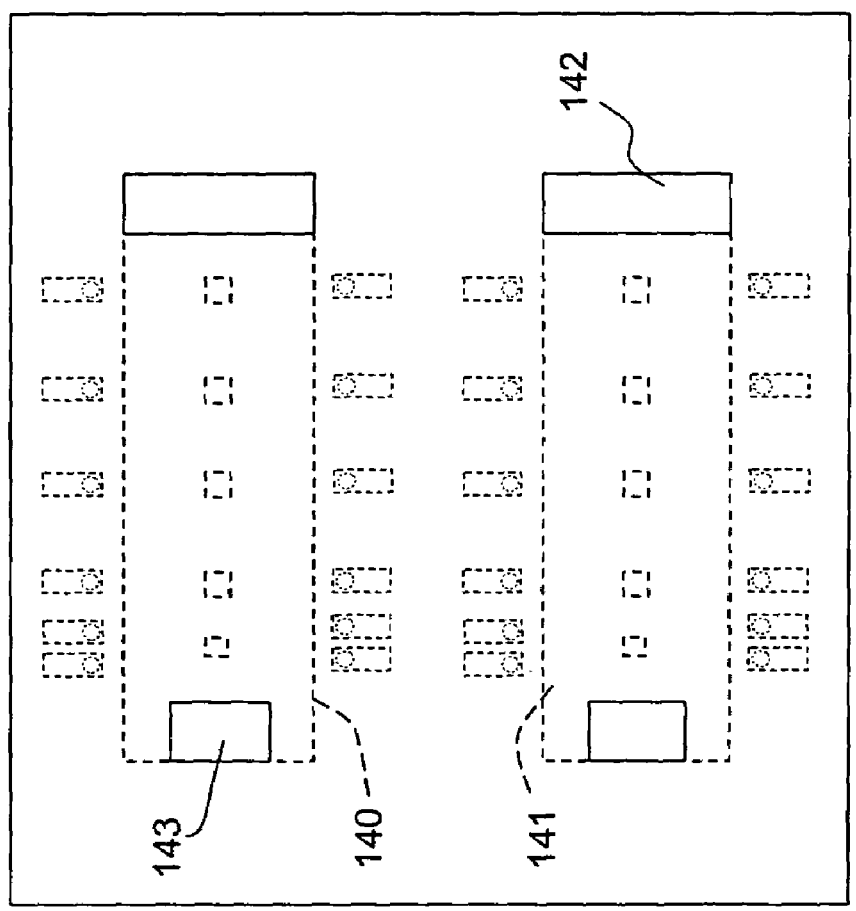
Figure 22:
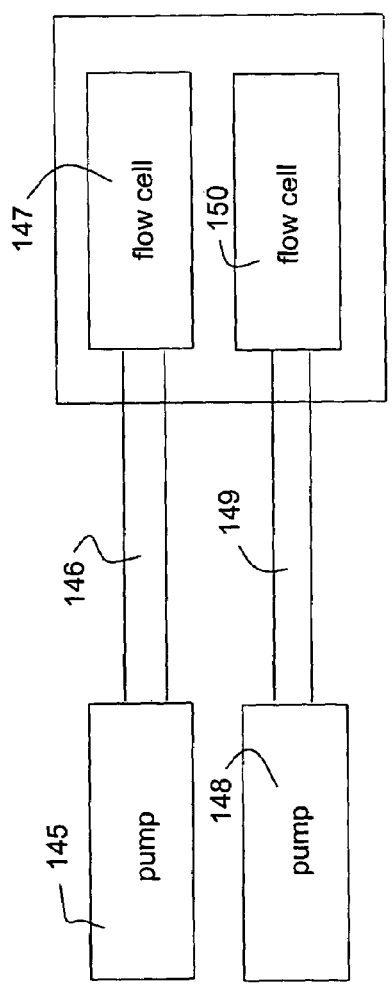
Figure 23:
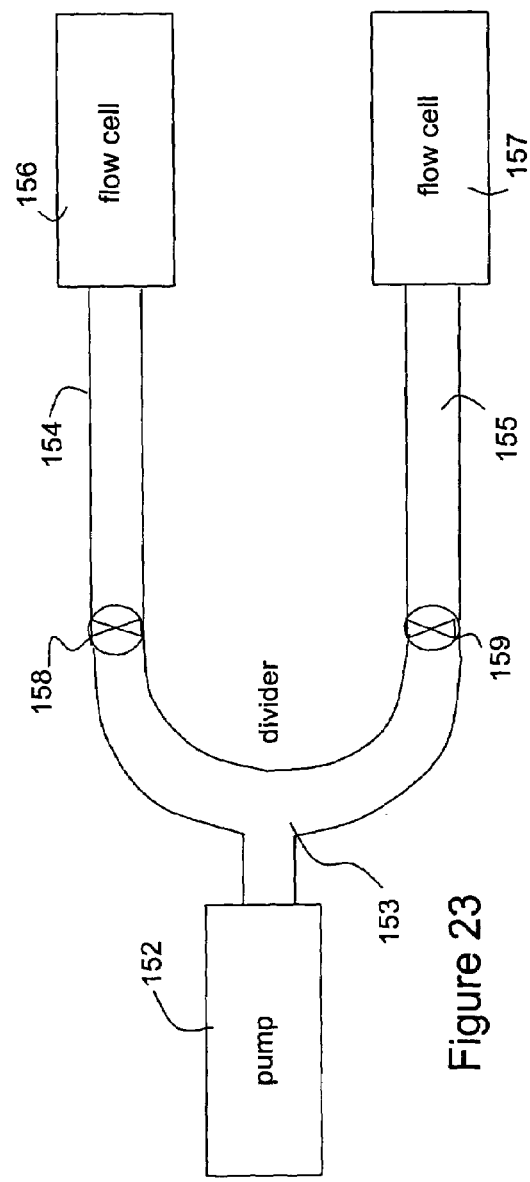
Figure 24:
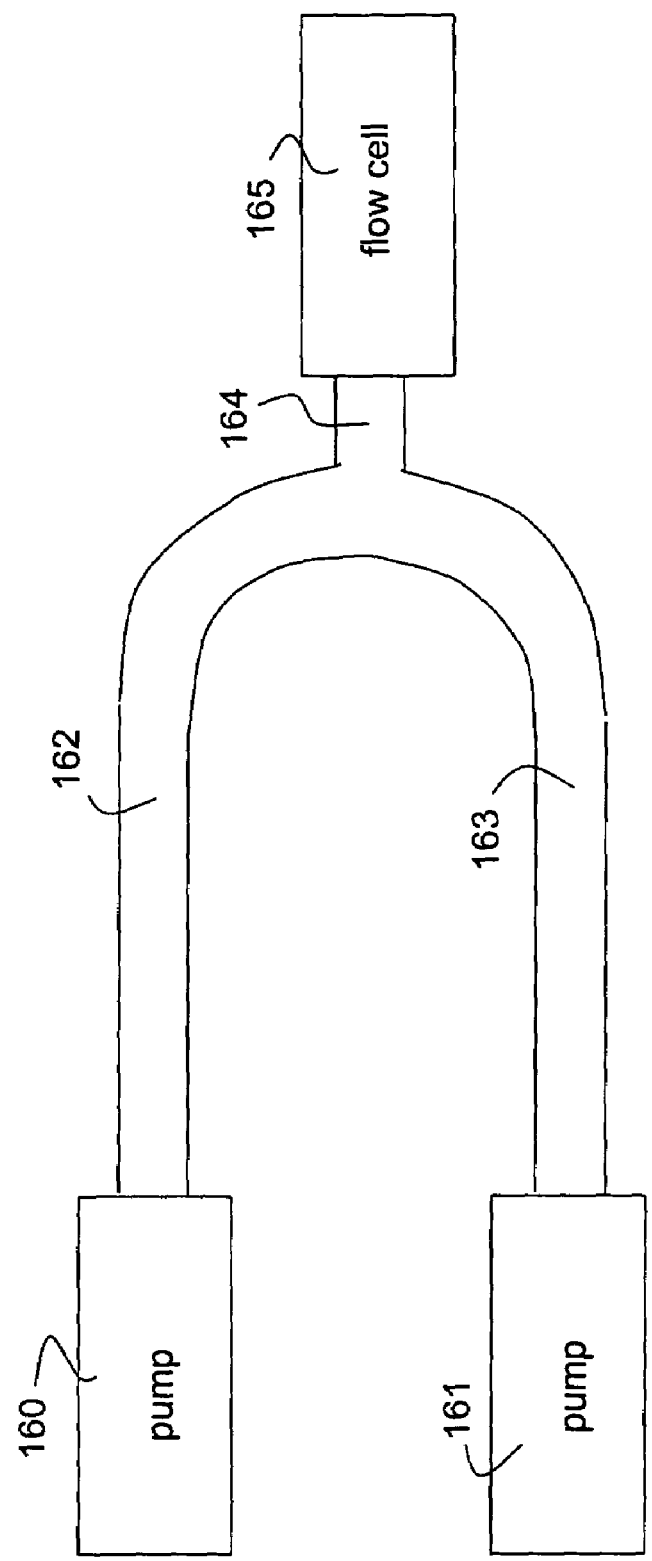

The best mode presently contemplated for carrying out the invention is illustrated in the accompanying drawings, in which:

FIG. 1 is a top plan view of a micro slit flow cell of the invention;

FIG. 2, a vertical section of the flow cell of FIG. 1, taken on the line 2-2 of FIG. 1;

FIG. 3, a vertical section of an alternative channel entrance and exit configuration for a slit flow cell;

FIG. 4, a top plan view of a flow channel substrate;

FIG. 5, a vertical section of the flow channel substrate of FIG. 4, taken on the line 5-5 of FIG. 4;

FIG. 6, a series of vertical sections showing the process sequence to form cavities on a substrate with SOI wafer;

FIG. 7, a top plan view of a monolithic pressure sensor array;

FIG. 8, a vertical section of the monolithic pressure sensor array of FIG. 7, taken on the line 8-8 of micro slit flow cell of FIG. 7;

FIG. 9, an enlarged fragmentary vertical section of an individual pressure sensor showing a cavity and thin membrane section;

FIG. 10, a top plan view of a pattern on the pressure sensor substrate for a monolithic pressure sensor array;

FIG. 11, a vertical section of the pressure sensor substrate of FIG. 10, taken on the line 11-11 of FIG. 10;

FIG. 12, a top plan view of the pattern on the pressure sensor membrane at the interface with the pressure sensor substrate;

FIG. 13, a vertical section of the pressure sensor membrane of FIG. 12, taken on the line 13-13 of FIG. 12;

FIG. 14, a vertical section of an alternative design of monolithic pressure sensor arrays;

FIG. 15, a top plan view of a piezoresistor pattern on the silicon membrane for pressure measurement;

FIG. 16, a vertical section of an alternative flow cell having a channel with portions of different sizes;

FIG. 17, a perspective view of a further embodiment of a slit rheometer with a channel having portions of different sizes;

FIG. 18, a vertical section of the slit rheometer of FIG. 17 taken on the line 18-18 of FIG. 17;

FIG. 19, a top plan view of a still further embodiment of slit rheometer with a channel having portions of different sizes;

FIG. 20, a vertical section of the slit rheometer of FIG. 19 taken on the line 20-20 of FIG. 19;

FIG. 21, a top plan view of a slit rheometer having multi channels positioned side by side;

FIG. 22, a block diagram of a slit rheometer system showing parallel flow cells and pumps;

FIG. 23, a block diagram of a slit rheometer system having a single pump connected to two flow cells; and FIG. 24, a block diagram of a slit rheometer system for mixing test liquids having two pumps feeding a single flow cell.

DETAILED DESCRIPTION OF THE ILLUSTRATED EMBODIMENT

An embodiment of a micro slit flow cell of the invention is shown in FIGS. 1 and 2 and includes a flow entrance or inlet 20, a flow exit or outlet 21, and a flow channel 22 therebetween. The flow channel 22 has a predetermined uniform depth (gap) in the micrometer range along the channel. The width of the channel is significantly larger than the depth of the channel so that the flow through the channel can be considered to be a one-dimensional problem instead of a two dimensional problem. The ratio of the width to the depth is preferably larger than ten. The preferred depth of the channel is in the order of a micrometer. The preferred length of the channel is at least one hundred micrometers excluding the entrance and exit zones, 23 and 24, respectively. In order to measure the true viscosity of a test liquid, the test liquid is forced to flow through the flow channel 22 of the micro slit flow cell by a pumping system, not shown, at a controllable constant volumetric flow rate. Because of the small volume required by the micro flow cell, a pumping system for small volumes is preferably used. A micro syringe pump is one of several possible pumping system. Micro syringe pumps are readily available and a selected micro syringe pump, not shown, is connected to the inlet 20 of the flow cell in a known manner. A drain or drain system, also not shown, is connected to the exit or outlet 21 in a known manner.

When the test liquid flows in flow channel 22, pressure drops along the flow direction indicated by arrow 25. The pressure drop indicates the steady state shear stress of the test liquid flowing in the flow channel 22 if pressure is measured sufficiently away from the entrance zone 23 and the exit zone 24 so that a constant pressure drop is measured for a fully developed flow. For the pressure drop measurement, pressure sensors are located in pressure sensor cavities 26 positioned at different locations along the flow channel 22 away from the entrance and the exit zones. The pressure sensors measure the pressure of the flowing liquid in the flow channel 22 at the location of the respective cavity 26. Preferably, at least two pressure sensor cavities 26 with associated pressure sensors are positioned along the flow channel 22, four such pressure sensor cavities being shown in FIGS. 1 and 2. Liquid viscosity is known to be very sensitive to temperature. Therefore it is necessary to maintain a substantially uniform temperature across the flow channel for accurate viscosity measurements. Also the temperature of the liquid being tested needs to be known. It is thus preferred to measure the temperature of the test liquid flowing through the flow channel. For this reason, a temperature sensor cavity 28 is located along the flow channel near the entrance zone. If desired, an additional temperature sensor cavity, not shown in FIGS. 1 and 2, can be located near the exit zone to monitor the temperature uniformity or provide temperture change information to be used in correcting the viscosity measurements obtained. At the bottom of the flow cell, bond pads 29 are located in a manner so that the necessary electrical connections to the pressure sensors, temperature sensors, and other sensors that may be provided can be made in a simple manner, for example to a microcontroller based PCB (printed circuit board) read out circuit through wire bonding or other surface mounting technology. Flow into the entrance 20 and from the exit 21 can be made to be perpendicular to the flow channel 22 as shown in FIG. 2, or parallel to the flow channel 22 as shown in FIG. 3, depending on the desired channel and cell configurations and interfaces with the pumping system at the entrance and with the drain system at the exit.

The flow cell includes a flow channel substrate 30 and a sensor plate formed of a sensor membrane 31 and a sensor substrate 32. The flow channel substrate 30 has a cavity 33, FIGS. 4 and 5, which forms the flow channel 22 when the substrate is combined with the sensor plate, as shown in FIGS. 2 and 3. The flow channel substrate 30 may also have an inlet hole 34 which forms the channel entrance 20 and an outlet hole 35 which forms the channel exit 21. The sensor membrane 31 forms a monolithic, substantially smooth flow channel pressure sensing surface 36 along one side of the flow channel 22, shown as the bottom channel surface in the orientation of FIGS. 2 and 3. The pressure sensors and temperature sensors are preferably integrated into the sensor plate so a monolithically integrated array of pressure sensors with one or more temperature sensors is formed. The monolithic pressure sensing surface 36 provides a sufficiently smooth flow channel pressure sensing surface to provide more accurate pressure measurements and potentially longer service than if the pressure sensors were individually and separately placed on or in the pressure sensing surface.

The flow channel substrate 30 has a cavity 33 with well defined pre-determined depth as shown in FIG. 4 and 5. In this cavity 33, the width is much bigger than the depth. The cavity can be formed by etching the substrate after photoresist on the substrate is patterned using the known photolithography processes of micro-fabrication processes. The etching method can be wet chemical etching or plasma dry etching. These etching processes are made on a wafer level so that many cavities can be formed simultaneously. For the wafer, borosilicate glasses (Pyrex 7740), Silicon, GaAs, or other materials used in microfabrication processes can be used. Etching of these wafers can be done in a known manner. If Pyrex is used for the substrate 30, the Pyrex is etched with buffered hydro fluoric acid solution or Buffered Oxide Etcher (BOE) to form the cavity 33. The inlet or entrance hole 34 and the outlet or exit hole 35 can be made by ultrasonic cutting, other mechanical machining, or by etching.

FIG. 6 shows an alternate method for forming the flow cavity 33 in the flow channel substrate 30. First a Pyrex wafer 40 with holes, not shown, for the entrance and exit is bonded to the device silicon 41 of an SOI (silicon-on-insulator) wafer, which consists of device silicon 41, buried oxide 42, and handle silicon 43, using conventional nomenclature. This is shown in 6A. Then the handle silicon 43 is etched away to give the wafer formation of 6B. The exposed oxide layer 42 is patterned as at 44, 6C, for subsequent etching of the device silicon layer 41 to form a cavity 45, 6D. Then the oxide layer is removed to give the flow channel substrate of 6E. Alternatively, the cavity can be formed on a silicon wafer by first oxidizing the silicon. The oxide is patterned to form etch masks. Then the exposed silicon is etched to form cavities in a known manner. The remaining oxide is removed subsequently.

The sensor plate consists of pressure sensor membrane 31 and a pressure sensor substrate 32. At the interface between the membrane 31 and the substrate 32, there are cavities for pressure sensing and for temperature sensing. The cavities can be formed in the back or underside of the pressure sensor membrane, in the pressure sensor substrate, or in both. The portion of the membrane which extends over each cavity deflects as pressure is applied to the pressure sensing surface 36 over the cavity and the amount of deflection of the membrane into the cavity is measured to provide an indication of the pressure applied to the pressure sensing surface over the cavity. FIGS. 2, 3, 8, and 9 show pressure sensor cavities 26 and temperature sensor cavities 28 formed in the back or underside of the pressure sensor membrane 31. The deflection of the portion of the pressure sensor membrane that extends over a cavity, indicated as 48 in FIG. 9, can be measured by a capacitance change, resistance change, optical path change, or other type pressure sensor, as desired.

FIG. 9 shows a capacitacnce pressure sensor which measures a capacitance change as the portion of the membrane 48 over the pressure sensor cavity 26 deforms under different pressures applied by a test liquid flowing over membrane portion 48. In this embodiment, cavity 26 has two sides, 50 and 51, and each side 50 and 51 has an electrode 52 and 53, respectively, mounted thereto. An insulating layer 54 separates upper electrode 52 from the pressure sensor membrane material, while lower electrode 53 is mounted directly to the pressure sensor substrate. Insulating material 55 is provided on the upper face of capacitor lower electrode 53 to prevent shorting of the electrodes under pressure that would deform the membrane portion 48 to cause electrode 52 to otherwise contact electrode 53. The capacitance of the two electrodes depends upon the separation of the electrodes and changes as the gap or distance between the electrodes change as the membrane portion 48 over the cavity deflects under pressure.

The sensor plate is fabricated on a wafer using microfabrication processes. The pressure sensor substrate 32 can be prepared by processing a Pyrex wafer as shown in FIGS. 10 and 11. Chrome or Titanium, and Platinum are deposited in sequence and are patterned to form temperature sensors 57 on the surface of the Pyrex. Bottom capacitor electrodes 53 and electrical leads 58 are formed by depositing metal on patterned resist on the Pyrex. The resist is lifted off to leave patterned metals. If desired, the Pyrex can be etched slightly before depositing metals using the patterned resist as etch mask so that most of the metals deposited are embedded in the Pyrex. Oxide is then deposited over the capacitor electrodes to form insulating material 55. The Pyrex can be ultrasonically machined to form vias 60.

The pressure sensor membrane can be made using an SOI wafer, for example. As indicated in connection with FIG. 6, and referring to FIG. 6, an SOI (silicon-on-insulator) wafer consists of device silicon 41, buried oxide 42, and handle silicon 43. The SOI wafer does not include the pyrex 40 shown in FIG. 6A. In using an SOI wafer for fabricating the sensor membrane, the device silicon, which becomes the pressure sensor membrane material 31, is etched to form the desired pressure sensor cavities 26 and temperature sensor cavities 28 on the underside of the membrane using patterned oxide as an etch mask. The oxide is then removed and a fresh oxide layer to form insulating material 54 is grown on the device silicon. Metal is then deposited on patterned resist on the oxide layer over the device silicon of the SOI. The resist is removed to form the capacitor upper electrodes 52 and to form electrical leads 61, FIG. 13, separated from the device silicon 31 by the insuling oxide layer 54.

The processed SOI wafer for forming the pressure sensor membrane is then bonded to the processed Pyrex wafer forming the pressure sensor substrate. Metal is then deposited using an aperture mask on the bottom of the pyrex pressure sensor substrate to form the bond pads 29, FIG. 11, and electrical connectivity 62 along vias 60 to connect with leads 58. The handle silicon and buried oxide layer of the SOI wafer forming the membrane is then removed in sequence to finish formation of the pressure sensor plate.

FIG. 14 shows a pressure sensor cavity 64 formed in the pressure sensor substrate 65 rather than in the pressure sensor membrane 66. A capacitor upper electrode 67 and electrical lead 68, and an insulating layer 69, are formed on the flat bottom surface (no wells) of the pressure sensor membrane 66. Capacitor lower electrode 70 and electrical lead 71 are formed in the well 64 and on the surface of the pressure sensor substrate 65. Insulating material 72 is deposited on capacitor lower electrode 70. This forms a pressure sensor plate similar to that described for prior figures, and operates similarly to detect and measure the deflection of membrane 66 into cavity 64. The difference is that the pressure sensor cavity is formed in the pressure sensor substrate rather than in the pressure sensor membrane, and the pressure sensor membrane will be of a uniform thinner thickness. The temperature sensor cavities in this embodiment will similarly be formed in the substrate rather than in the membrane.

If piezoresistivity is employed for pressure measurement, the semi-conductor membrane (membrane portion 48 in FIG. 9 and membrane 66 in FIG. 14) is properly doped in a known manner to form resistors 75, FIG. 15, where the membrane is indicated as 76. The resistance changes of the doped resistors 75 on the membrane 76 as the membrane is deflected into a cavity, are measured in a known manner. As the membrane deflects due to pressure, resistances of the doped regions change and the changes are measured in, for example, a Wheatstone-bridge configuration of the resistors. For example, p-type piezoresistors are formed along the <110> directions on an n-type (100) silicon wafer 76 as shown in FIG. 15. These conventional piezo-resistive silicon sensors are not suitable for high temperature applications above 120° C. With temperatures above 120° C., the p-n junctions leaks current. In order to prevent the current leakage and increase the service temperature for these conventional piezo-resistive silicon sensors, the p-n junctions can be isolated by putting insulators between the p-n junctions or using a SOI (silicon-on-insulator) in a known manner. Alternately, wide band gap materials such as GaAs or SiC can be used for the membrane materials.

After fabrication of the pressure sensor plate and the flow channel substrate as described above, the combined wafers forming the pressure sensor plate and the wafer forming the flow channel substrate are then joined and bonded together in a known manner depending on the chosen material combinations for the pressure sensor plate and the flow channel substrate to form a wafer with completed micro flow cells as shown in FIGS. 1, 2, and 3. The bonding method could be glass-frit, thermal compression, eutectic bonding, anodic bonding, or other methods. Using micro-fabrication processes, such as those described as examples, many flow cells can be made on a single combined wafer, and many such wafers can be made in a batch, all in a very cost effective manner. Since many flow cells can be made on each wafer, the combined wafer forming the completed flow cells can be diced to separate the flow cells into individual flow cells or into pieces containing a desired number of individual flow cells.

Alternatively, a wafer with flow channel substrates is bonded first with the SOI wafer. Then the handle Si and oxide are sequentially removed. The exposed device Si wafer is processed to form a plurality of sensor membranes. A Pyrex 7740 wafer with plurality of pressure sensor substrates is separately processed. Then the two wafers are combined preferably with an anodic bonding process. The bonded wafers are then diced for individual viscosity sensors after vias are processed appropriately.

Each flow cell may also have multiple flow channels in series with varying widths or with varying gaps as shown in FIG. 16. FIG. 16 shows the flow channel with two different sized gaps 80 and 81 in series in the specific construction of the flow cells as described herein. Pressure sensor cavities 82 are located to allow pressure sensing for fluid flowing in the portion of the channel with gap 80, while pressure sensor cavities 83 are located to allow pressure sensing for fluid flowing in the portion of the channel with gap 81. Temperature sensor cavity 84 allows temperature measurement at the beginning of the portion of the channel with gap 80 and temperature sensor cavity 85 allows temperature measurement at the beginning of the portion of the channel with gap 81. Additional temperature sensor locations can also be provided such as at the outlet end of the portion of the channel with gap 81. The same fabrication techniques are used for forming the channels and pressure sensing plate as described for the previous embodiments with a channel of constant volume, but with modifications in the etching, machining, and/or other channel forming steps to form the channel with two or more different gaps or widths. Such modifications would be obvious to one skilled in the fabrication techniques used after a study of the description herein so far. FIGS. 17-20 show more generally a slit rheometer of the invention having a flow channel with two or more different flow volumes arranged in series.

FIGS. 17 and 18 a slit rheometer of the invention with a rheometer body constructed of a bottom portion 120 and a top portion 121. The bottom portion 120 has at least two recessed sections, three recessed sections 122, 123, and 124 being shown, with varying depth h, FIG. 18, and fixed width. The recesses form a channel for liquid flow. The top portion 121 is a pressure sensor plate of the invention and includes an array of pressure sensors 125, FIG. 17, and indicated as cavities 126 in FIG. 18, spaced in such a way that at least two sensors 125 are located to measure pressures at at least two different positions in each recessed section, 122, 123, and 124. Each recessed section is sufficiently long to ensure a fully developed flow inside of each section. The sensors are positioned to measure the pressure of the fully developed flow. The pressure sensor substrate 121, as best seen in FIG. 18, has an opposite orientation to that shown in FIG. 16. What has been referred to as the pressure sensor membrane is wafer 121a orientated to form the bottom of the pressure sensor plate with the measuring surface facing downwardly into the liquid flow channel, and what has been referred to as the pressure sensor substrate is 121b oriented to form the top of the pressure sensor plate. As is evident, the pressure sensor plate of the invention can be used in any orientation.

The preferred material for the bottom portion 120 is silicon, glasses, or other materials that are sufficiently rigid and are used in semiconductor or microelectromechanical processes and that can be processed with wet chemical etching, dry plasma etching, or hot embossing, or the combination of these. The bottom portion 120 can be also made of multiple layers if desired to form channels 122, 123, and 124. The width of the channel is significantly larger than the gap h of the channel in order to minimize the effect of the two sides of rectangular channels, and is preferably greater than ten times the gap at all channels 122, 123, and 124. The top portion 121 and the bottom portion 120 are constructed separately and then combined together with electrostatic bonding (anodic bonding) methods, low temperature glass bonding methods, eutectic bonding methods, or other methods depending on the materials or design.

FIGS. 19 and 20 show a slit rheometer constructed of a bottom portion 130 and a top portion 131. The bottom portion has at least two recessed sections, three recessed sections 132, 133, and 134 being shown, with varying width w and fixed depth. The recesses form a channel for liquid flow. The top portion 131 is a pressure sensor plate of the invention and includes an array of pressure sensors 135, FIG. 19, indicated as wells 136 in FIG. 20, spaced in such a way that at least two sensors 135 are located to measure pressures at at least two different positions in each recessed section 132, 133, and 134. Each section is sufficiently long to ensure a fully developed flow inside of each section. The sensors are positioned to measure the pressure of the fully developed flow. The channels are constructed in such a way that the width w to the gap ratio of each channel is sufficiently greater than ten in all channels.

With each of the slit rheometers shown, in use, a means to cause flow of liquid to be tested through the flow passage formed by the recesses in the slit rheometer is used to create liquid flow. Such means may be a pump or other source of pressurized liquid to be tested. During flow of liquid, the pressure exerted by the liquid at the locations of the pressure sensors is measured by each sensor and from such measurements the apparent viscosity and true viscosity may be determined in known manner.

The orientation of the larger and smaller flow passages formed by the differently dimensioned recesses is shown as opposite in FIGS. 17 and 19. It will not make any difference which way the flow of liquid takes place through the slit or flow channel. The important flow property that is measured to determine apparent viscosity is the difference in pressure sensed by the two sensors in a particular dimensioned recess. Comparison of the measurements in differently dimensioned recesses is used to determine the exact or true viscosity of the liquid. While two differently dimensioned recesses will provide a reasonably accurate indication of exact viscosity, the more recesses present the better the accuracy. The presence of two or more recesses also allows the measurement of viscosity at multiple shear rates with one measurement. However, increased accuracy is offset by increased expense for more recesses. With the integrated recesses of the slit rheometers of the invention, the cost for increased recesses is reduced over the prior art where separate devices with different size slits were used, but there is still an increased cost for increased recesses. Excellent accuracy within the usually desired range can generally be obtained with two or three recesses.

For true viscosity measurement, rather than the flow channel having at least two sections in series with different flow volumes, each flow cell may have two or more flow channels in parallel as shown in FIG. 21. FIG. 21 shows two parallel flow cells 140 and 141. Such flow cells can be formed by dicing the wafer containing the flow cells so that a diced piece includes two or more parallel cells. Where two or more flow cells are used, separate pumps may be used for each different cell. This is shown schematically in FIG. 22. Pump 145 pumps test liquid through conduit 146 to cell 147.

Pump 148 pumps test liquid through conduit 149 to cell 150. If the channels of the cells are the same size and the same test fluid is used in each cell, true viscosity can be measures by running pump 145 to pump fluid at one rate through flow cell 147 and running pump 148 to pump the fluid at a different rate through cell 150. The pressure measurement obtained from each cell are compared to obtain and correlated with the flow rate to obtain the true viscosity. Of course, if using only one pump and one flow cell, if the flow rate of the pump can be adjusted, a test liquid can be run through the cell with the pump operating at one flow rate and then the flow rate can be changed and pressure measurements taken for the same test liquid being pumped through the cell at the different flow rate. If one pump is used, then a valve or valves can be used to direct flow to one or another cell. This is shown in FIG. 23. Pump 152 is connected through divider 153 and conduits 154 and 155 to cells 156 and 157 respectively. Valve 158 in conduit 154 controls flow to cell 156, while valve 159 in conduit 155 controls flow to cell 157. True viscosity can be measured by running the pump at constant flow rate and switching between flow cells if the flow channels of the flow cells are of different size. With the same size flow channels in the cell, true viscosity can be measured if the valves 158 and 159 are replaced by flow controllers so that flow from the pump will simultaneously flow at controlled known rates through both cells 156 and 157. Alternately, parallel flow cells can be connected appropriately with flow channels or conduits, or other connections, to form channels connected in series. Thus, the outlet 142 of channel 141 may be connected to the inlet 143 of channel 140 in FIG. 21. Such series connected channels may have different channel sizes so that, in effect, a series channel of different sizes or flow volumes is created.

In some cases it is desirable to measure the viscosity of a mixture of liquids. In such case, separate pumps can be provided for each liquid to be mixed, such as pumps 160 and 161 in FIG. 24, with the output conduits 162 and 163 from each pump being joined so that the liquids from each pump mix in conduit 164 directing the mixed liquids to cell 165. The ratio of the mixed components is controlled by controlling the relative pumping rate of the two pumps 160 and 161.

It should be remembered that in measuring viscosity, a constant flow rate through the channel is important. Therefore, the various flow conduits described connecting pumps to flow channels or connecting multiple flow channels should be rigid enough to prevent stretching and bulging that could cause liquid flow through the channels to vary.

Inventions described in FIGS. 1, 7, 10, 15, and 16 have bond pads located at the bottom of the pressure sensor substrate so that the bond pads are connected to the detection circuitries. However, this bond pad configuration may not be desirable for certain applications. Instead, the bond pads may be positioned on the top of the pressure sensor substrates beyond flow channels so that they are exposed. The exposed pads are wire bonded further to the detection circuitry. To make this bond pad configuration, the conductor leads fabricated on the pressure sensor membrane should be properly transferred to bond pads on the top of the pressure sensor substrate.

This viscosity sensor can be further integrated with a flow rate sensor. The flow sensor measures the flow rate of liquid and the viscosity sensor measures a pressure drop along the flow channel. With the known flow rate and the pressure drop, apparent viscosity can be measured. In order to measure the true viscosity, pressure drops need to be measured for different flow rates. This can be achieved by connecting flow channels with different gaps or by varying flow rates. As the liquid flows through the flow channels, flow rates vary in each channel because of the change in cross-section. The variation in flow rate changes the pressure drop in each channel. From the measured pressure drop for each channel, a true viscosity can be obtained. The flow rate sensors that can be used along with the viscosity sensor are hot wire flow rate sensor, acoustic wave flow rate sensor, coriolis flow rate sensor, etc. These sensors are constructed and integrated in a known manner.

Additional details of the pressure sensor plate construction and details of other detectors are contained in parent application Ser. No. 10/286,602, now U.S. Pat. No. 6,892,583.

Whereas this invention is here illustrated and described with reference to embodiments thereof presently contemplated as the best mode of carrying out the invention in actual practice, it is to be realized that various changes may be made in adapting the invention to different embodiments without departing from the inventive concepts disclosed herein.

What is claimed is:

1. A slit rheometer for determining the viscosities of liquids comprising:
   a monolithic sensor plate formed from a combination of a pressure sensor membrane and a pressure sensor substrate having at least two cavities formed in one or the other or both of the pressure sensor membrane and the pressure sensor substrate, a portion of the pressure sensor membrane extending over respective cavities of the at least two cavities whereby the portions of the pressure sensor membrane extending over the respective cavities will deflect into the respective cavities upon application of pressure to the portion of the pressure sensor membrane over a respective cavity, the amount of deflection being proportional to the pressure applied to the membrane over the respective cavity, and a pressure sensor formed in each of the plurality of cavities to provide the monolithic sensor plate with a substantially smooth surface and a plurality of independent pressure sensors in the monolithic sensor plate;
   a channel substrate configured to form at least one flow channel therein when combined with the monolithic sensor plate with the at least one flow channel having a flow entrance and a flow exit; and
   each of said at least one flow channel having at least two individual pressure sensors located therein and spaced sufficiently away from the liquid entrance and the liquid exit whereby a pressure drop of fully developed flow of liquid through the at least one flow channel can be measured.

2. A slit rheometer according to claim 1, additionally including means to force a liquid to flow through the at least one flow channel at a known volumetric flow rate.

3. A slit rheometer according to claim 1, wherein the at least one flow channel has a width and a depth and wherein the width of the flow channel is at least about ten times larger than the depth of the flow channel in each of the at least one flow channels.

4. A slit rheometer according to claim 1, wherein the sensor plate has at least one temperature sensor for each of the at least one flow channels located to measure the temperture of the liquid flowing through the flow channel.

5. A slit rheometer according to claim 1, wherein there are at least two flow channels connected in series.

6. A slit rheometer according to claim 5, wherein the at least two flow channels connected in series each have a channel width and a channel depth, and wherein the at least two flow channels connected in series are different in channel depth.

7. A slit rheometer according to claim 5, wherein the at least two flow channels connected in series each have a channel width and a channel depth, and wherein the at least two flow channels connected in series are different in channel width.

8. A slit rheometer according to claim 1, wherein there are at least two channels connected in parallel.

9. A slit rheometer according to claim 1, where the at least one channel is on the order of a micrometer in depth.

10. A slit rheometer according to claim 9, where the at least one channel is at least about ten micrometers in width.

11. A slit rheometer according to claim 10 where the at least one channel has a length of at least about one hundred micrometers.

12. A slit rheometer according to claim 1 where the pressure sensors are capacitive pressure sensors.

13. A slit rheometer according to claim 1, wherein the channel substrate is combined with the monolithic sensor plate along one surface of the channel substrate, and wherein the channel substrate has at least one channel cavity formed therein opening along the one surface of the channel substrate so that when the channel substrate is combined with the monolithic sensor plate, the monolithic sensor plate closes the at least one channel cavity along the one surface of the channel substrate to form the at least one flow channel.

14. A slit rheometer according to claim 13, wherein the at least one channel cavity has opposite ends and the flow entrance extends through the channel substrate to one end of the channel cavity and the flow exit extends through the channel substrate to the opposite end of the channel cavity.

15. A slit rheometer according to claim 13, wherein each of the at least one channel cavity includes three channel walls and wherein the monolithic sensor plate froms a fourth wall for each of the at least one channel cavity when the monolithic sensor plate is combined with the channel substrate to form the at least one flow channel.

16. A slit rheometer according to claim 1, wherein channel substrate is at least a portion of a wafer of a material used in microfabrication processes.

17. A slit rheometer according to claim 1, wherein the pressure sensor membrane is at least a portion of a silicon wafer.

18. A slit rheometer according to claim 1, wherein the pressure sensor substrate is at least a portion of a wafer of a material used in microfabrication processes.

19. A slit rheometer according to claim 18, wherein the wafer of a material used in microfabrication processes is a borosilicate glass wafer.

20. A slit rheometer according to claim 1, wherein the pressure sensor formed in each of the plurality of cavities is a single sensor cooperable with the portion of the pressure sensor membrane extending over the respective cavity to sense the deflection of such portion and provide a signal indicative of a single deflection sensed for the respective cavity.

21. A method of manufacturing slit rheometers comprising:
forming at least two cavities in one or both of a pressure sensor membrane and a pressure sensor substrate;
combining the pressure sensor membrane with the pressure sensor substrate to create a pressure sensor plate with a portion of the pressure sensor membrane extending over respective cavities of the at least two cavities;
forming independent pressure sensors in the at least two cavities; and
combining the pressure sensor plate with a channel substrate to create at least one flow channel having a flow entrance and a flow exit through which liquid can flow, the flow channel passing over at least two of the at least two independent pressure sensors in the pressure sensor plate with the at least two independent pressure sensors spaced sufficiently away from the liquid entrance and the liquid exit whereby a pressure drop of fully developed flow of liquid through the at least one flow channel can be measured.

22. A method of manufacturing slit rheometers according to claim 21 where the at least two cavities formed in one or both of the pressure sensor membrane and the pressure sensor substrate are formed by etching using chemical etching.

23. A method of manufacturing slit rheometers according to claim 21 where the at least two cavities formed in one or both of the pressure sensor membrane and the pressure sensor substrate are formed by etching using plasma etching.

24. A method of manufacturing slit rheometers according to claim 21 where the at least two cavities formed in one or both of the pressure sensor membrane and the pressure sensor substrate are formed by etching using a combination of chemical and plasma etching.

25. A method of manufacturing slit rheometers according to claim 21 where the pressure sensors are capacitor type sensors.

26. A method of manufacturing slit rheometer according to claim 21 where the pressure sensors are piezoresistive type sensors.

* * * * *